United States Patent
Deguchi et al.

(10) Patent No.: US 9,157,158 B2
(45) Date of Patent: *Oct. 13, 2015

(54) METHOD FOR PRODUCING ALCOHOL

(71) Applicants: Masahiro Deguchi, Osaka (JP); Hiroshi Hashiba, Osaka (JP); Satoshi Yotsuhashi, Osaka (JP); Yuka Yamada, Nara (JP)

(72) Inventors: Masahiro Deguchi, Osaka (JP); Hiroshi Hashiba, Osaka (JP); Satoshi Yotsuhashi, Osaka (JP); Yuka Yamada, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 5 days.

This patent is subject to a terminal disclaimer.

(21) Appl. No.: 14/450,999

(22) Filed: Aug. 4, 2014

(65) Prior Publication Data

US 2014/0367271 A1 Dec. 18, 2014

Related U.S. Application Data

(63) Continuation of application No. PCT/JP2013/004051, filed on Jun. 28, 2013.

(30) Foreign Application Priority Data

Jul. 5, 2012 (JP) ................... 2012-151092

(51) Int. Cl.
*C25B 3/04* (2006.01)
*C25B 9/08* (2006.01)
(Continued)

(52) U.S. Cl.
CPC . *C25B 3/04* (2013.01); *C07C 29/15* (2013.01); *C25B 1/003* (2013.01); *C25B 9/08* (2013.01); *C25B 9/166* (2013.01); *B01J 35/0033* (2013.01); *Y02E 60/366* (2013.01)

(58) Field of Classification Search
CPC ............ C25B 3/04; C25B 9/08; C25B 9/166; C25B 1/003; C07C 29/15; Y02E 60/366; B01J 35/0033
USPC ........................................ 204/157.9; 205/340
See application file for complete search history.

(56) References Cited

U.S. PATENT DOCUMENTS 7,750,234 B2 * 7/2010 Deng et al. ..................... 204/252
8,313,634 B2 * 11/2012 Bocarsly et al. .............. 205/440
(Continued)

FOREIGN PATENT DOCUMENTS

JP 55-105625 A 8/1980
JP 05-311476 A 11/1993
(Continued)

OTHER PUBLICATIONS

Yotsuhashi et al, Applied Physics Letters, vol. 100, No. 24, pp. 243904-1243904-3, 2012.
(Continued)

*Primary Examiner* — Keith Hendricks
*Assistant Examiner* — Colleen M Raphael
(74) *Attorney, Agent, or Firm* — McDermott Will & Emery LLP

(57) ABSTRACT

Disclosed is a method for producing an alcohol using a device for reducing carbon dioxide by light energy. In this device, a cathode electrode includes copper or a copper compound, and an anode electrode includes a region including a nitride semiconductor layer in which an $Al_xGa_{1-x}N$ layer ($0<x\leq1$) and a GaN layer are laminated. A first electrolytic solution consisting of an aqueous potassium chloride solution (aqueous KCl solution) is contained in a cathode chamber in which the cathode electrode is placed. A second electrolytic solution including an aqueous sodium hydroxide solution (aqueous NaOH solution) is contained in an anode chamber in which the anode electrode is placed.

11 Claims, 3 Drawing Sheets

(51) Int. Cl.
*C25B 1/02* (2006.01)
*C07C 29/15* (2006.01)
*C25B 1/00* (2006.01)
*C25B 9/16* (2006.01)
*B01J 35/00* (2006.01)

(56) References Cited

U.S. PATENT DOCUMENTS

| | | | |
|---|---|---|---|
| 8,652,989 B2 | 2/2014 | Sato et al. | |
| 8,696,883 B2 | 4/2014 | Yotsuhashi et al. | |
| 2011/0203661 A1* | 8/2011 | Taniguchi et al. | 136/258 |

FOREIGN PATENT DOCUMENTS

| | | | |
|---|---|---|---|
| JP | 6-126189 A | 5/1994 | |
| JP | 7-188961 A | 7/1995 | |
| JP | 2003-275599 A | 9/2003 | |
| JP | 2004-059507 A | 2/2004 | |
| JP | 3730142 B2 | 12/2005 | |
| JP | 2010-064066 A | 3/2010 | |
| JP | 2011-094194 A | 5/2011 | |
| WO | 2006/082801 A1 | 8/2006 | |
| WO | 2012/046374 A1 | 4/2012 | |

OTHER PUBLICATIONS

Denki Kagaku (Electrochemistry), vol. 58, No. 11, pp. 984-989, 1990 (Partial English abstract).

Noda et al, Chemistry Letters, 1989, pp. 289-292.

International Search report issued in Application No. PCT/JP2013/004051 dated Aug. 27, 2013.

* cited by examiner

METHOD FOR PRODUCING ALCOHOL

This is a continuation of International Application No. PCT/JP2013/004051, with an international filing date of Jun. 28, 2013, which claims the foreign priority of Japanese Patent Application No. 2012-151092, filed on Jul. 5, 2012, the entire contents of both of which are hereby incorporated by reference.

BACKGROUND OF THE INVENTION

1. Technical Field of the Invention

The present disclosure relates to a method for producing alcohols through carbon dioxide reduction reaction driven by light energy.

2. Description of Related Art

JP 05(1993)-311476 A, JP 07(1995)-188961 A, and WO 2012/046374 A1 each disclose a method for reducing carbon dioxide by light energy.

Specifically, in each of the methods disclosed in JP 05(1993)-311476 A and JP 07(1995)-188961 A, a semiconductor photoelectrode containing titanium oxide (titania, $TiO_2$) is used as an anode electrode (photoelectrode) for producing oxygen from water, and carbon dioxide is reduced by light irradiation of the anode electrode in combination with an external power source such as a solar cell or a potentiostat.

In the method disclosed in WO 2012/046374 A1, a semiconductor photoelectrode containing gallium nitride (GaN) is used as an anode electrode (photoelectrode), and carbon dioxide is reduced by light irradiation of the anode electrode alone.

JP 3730142 B2 discloses a method for photochemically decomposing water using a nitride semiconductor formed of AlInGaN and a laminate including the nitride semiconductor so as to produce hydrogen.

The methods disclosed in JP 05(1993)-311476 A and JP 07(1995)-188961 A require an external power source such as a solar cell or a potentiostat in addition to the cathode electrode and the anode electrode to reduce carbon dioxide.

In the method disclosed in WO 2012/046374 A1, carbon dioxide is reduced by light irradiation of the anode electrode to produce formic acid (HCOOH), carbon monoixde (CO), and others.

SUMMARY OF THE INVENTION

One non-limiting and exemplary embodiment provides a novel method for producing an alcohol through carbon dioxide reduction reaction driven by light energy alone and without using an external power source.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature a method for producing an alcohol using a device for reducing carbon dioxide by light energy. This method includes the steps of:

(a) preparing the device for reducing carbon dioxide, the device including a cathode chamber, an anode chamber, and a proton conducting membrane, wherein
the cathode chamber contains a cathode electrode,
the cathode electrode includes copper or a copper compound,
the anode chamber contains an anode electrode,
the anode electrode includes a region including a nitride semiconductor layer in which an $Al_xGa_{1-x}N$ layer ($0<x\leq 1$) and a GaN layer are laminated,
a first electrolytic solution consisting of an aqueous potassium chloride solution (aqueous KCl solution) is contained in the cathode chamber,
a second electrolytic solution including an aqueous sodium hydroxide solution (aqueous NaOH solution) is contained in the anode chamber,
the cathode electrode is in contact with the first electrolytic solution,
the anode electrode is in contact with the second electrolytic solution,
the proton conducting membrane is interposed between the cathode chamber and the anode chamber,
the first electrolytic solution contains carbon dioxide,
the cathode electrode is electrically connected to the anode electrode, and
a power source that is electrically connected to the cathode electrode and the anode electrode is not provided between the cathode electrode and the anode electrode; and (b) irradiating the anode electrode with light having a wavelength of 360 nm or less so as to reduce, at the cathode electrode, the carbon dioxide contained in the first electrolytic solution and to produce the alcohol.

It should be noted that general or specific embodiments may be implemented as a device, a system, a method, or any elective combination thereof.

The novel method for producing an alcohol according to the present disclosure produces the alcohol through carbon dioxide reduction reaction driven by light energy alone, without using an external power source provided between the cathode electrode and the anode electrode and electrically connected to these electrodes.

DETAILED DESCRIPTION

Findings Underlying the Present Disclosure

Figure 1A:
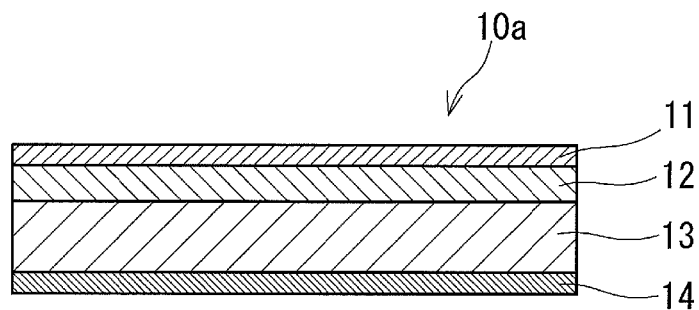
FIG. 1A to FIG. 1D are each a schematic view showing an example of the configuration of an anode electrode (photoelectrode) according to an embodiment of the present disclosure.

First, the findings underlying the present disclosure are described.

JP 05(1993)-311476 A and JP 07(1995)-188961 A report the use of the photoelectrochemical activity of a semiconductor material to reduce carbon dioxide, but this method may be problematic in that the use of an external power source such as a solar cell or a potentiostat is needed in addition to light irradiation of the anode electrode (photoelectrode).

WO 2012/046374 A1 reports the use of an improved anode electrode (photoelectrode) to reduce carbon dioxide by light energy alone, but this method may be problematic in that main reaction products are formic acid (HCOOH) and carbon monoxide (CO).

The present inventors used, as an anode electrode (photoelectrode) for use in an device for reducing carbon dioxide, an electrode including a region including a nitride semiconductor layer in which an $Al_xGa_{1-x}N$ layer ($0<x\leq1$) and a GaN layer are laminated, used, as a cathode electrode, an electrode including copper or a copper compound, and further used, as an electrolytic solution serving as a reaction field of carbon dioxide reduction, an aqueous potassium chloride solution (aqueous KCl solution) or an aqueous sodium chloride solution (aqueous NaCl solution) with an appropriate concentration, so as to increase the efficiency of the light energy-driven carbon dioxide reduction reaction and to control the reaction products obtained by the reduction of carbon dioxide.

As a result, the present inventors have found that alcohols can be produced by light irradiation of an anode electrode (photoelectrode) alone by developing a device capable of reducing carbon dioxide without the use of an external power source. The present disclosure has been accomplished based on these findings.

Description of Aspects of the Present Disclosure

Next, the aspects of the present disclosure are described.

The first aspect of the present disclosure provides a method for producing an alcohol using a device for reducing carbon dioxide by light energy. This method includes the steps of:

(a) preparing the device for reducing carbon dioxide, the device including a cathode chamber, an anode chamber, and a proton conducting membrane, wherein the cathode chamber contains a cathode electrode,
the cathode electrode includes copper or a copper compound,
the anode chamber contains an anode electrode,
the anode electrode includes a region including a nitride semiconductor layer in which an $Al_xGa_{1-x}N$ layer ($0<x\leq1$) and a GaN layer are laminated,
a first electrolytic solution including an aqueous potassium chloride solution (aqueous KCl solution) or an aqueous sodium chloride solution (aqueous NaCl solution) is contained in the cathode chamber,
a second electrolytic solution including an aqueous sodium hydroxide solution (aqueous NaOH solution) is contained in the anode chamber,
the cathode electrode is in contact with the first electrolytic solution,
the anode electrode is in contact with the second electrolytic solution,
the proton conducting membrane is interposed between the cathode chamber and the anode chamber,
the first electrolytic solution contains carbon dioxide,
the cathode electrode is electrically connected to the anode electrode, and
a power source that is electrically connected to the cathode electrode and the anode electrode is not provided between the cathode electrode and the anode electrode; and (b) irradiating the anode electrode with light having a wavelength of 360 nm or less so as to reduce, at the cathode electrode, the carbon dioxide contained in the first electrolytic solution and to produce the alcohol.

According to this aspect, it is possible to provide a novel method for producing an alcohol by light irradiation of the anode electrode (photoelectrode) alone through a simpler and more efficient carbon dioxide reduction reaction.

The second aspect of the present disclosure provides the method according to the first aspect, wherein a composition ratio of aluminum (a value of x) in the $Al_xGa_{1-x}N$ layer ($0<x\leq1$) of the anode electrode may be in a range of $0<x\leq0.25$.

According to this aspect, it is possible to effectively use the light irradiated to the anode electrode.

The third aspect of the present disclosure provides the method according to the first or the second aspect, wherein the GaN layer of the anode electrode may be n-type or $n^+$-type.

According to this aspect, it is possible to reduce the electrical resistance in the GaN layer and thus to reduce the ohmic loss.

The fourth aspect of the present disclosure provides the method according to any one of the first to third aspects, wherein an entire surface or a part of the surface of the $Al_xGa_{1-x}N$ layer ($0<x\leq1$) of the anode electrode may be coated with at least nickel oxide.

According to this aspect, it is possible to increase the oxygen production efficiency at the anode electrode through the so-called co-catalytic activity of nickel oxide.

The fifth aspect of the present disclosure provides the method according to the fourth aspect, wherein the nickel oxide may be in the form of fine particles.

According to this aspect, it is possible to coat the entire surface or a part of the surface of the $Al_xGa_{1-x}N$ layer of the anode electrode with nickel oxide with ease and high controllability.

The sixth aspect of the present disclosure provides the method according to any one of the first to fifth aspects, wherein in the step (b), the device for reducing carbon dioxide may be placed at room temperature and under atmospheric pressure.

According to this aspect, it is possible to easily produce alcohols through carbon dioxide reduction.

The seventh aspect of the present disclosure provides the method according to any one of the first to sixth aspects, wherein in the step (b), at least one of aldehyde, formic acid, carbon monoxide, hydrocarbon, and hydrogen may be obtained.

According to this aspect, it is possible not only to produce alcohols but also to obtain other reaction products at the same time through carbon dioxide reduction reaction driven by light energy.

Hereinafter, the embodiments of the present disclosure are described in detail. The following description relates to exemplary embodiments of the present disclosure, and the present disclosure is not limited to these embodiments.

(Anode Electrode (Photoelectrode))

FIG. 1A to FIG. 1D are each a schematic view showing an example of the configuration of an anode electrode (photoelectrode) according to the present disclosure. FIG. 1A is a diagram showing the basic configuration of the anode electrode (photoelectrode) used in the present disclosure. The anode electrode 10a is composed of an $Al_xGa_{1-x}N$ layer 11 ($0<x\leq1$) to be irradiated with light, a GaN layer 12, an electrically conductive substrate 13 used to form the nitride semiconductor layer, and an electrode portion 14 for electrically connecting the anode electrode 10a to a cathode electrode.

It is generally an effective method for fabricating this anode electrode 10a to form a thin film of the nitride semiconductor layer (the $Al_xGa_{1-x}N$ layer 11 and the GaN layer 12) on the conductive substrate 13, and the method is not particularly limited as long such a thin nitride semiconductor film can be formed on a substrate. For example, the method is metal-organic vapor-phase epitaxy. Specific examples of the conductive substrate 13 include a single-crystalline gallium nitride (GaN) substrate and a single-crystalline silicon (Si) substrate having low electrical resistance. The method for forming the electrode portion 14 on the conductive substrate 13 is also not be particularly limited, but the method is desirably vacuum deposition (such as resistance heating evaporation or electron beam evaporation) as a commonly used technique for forming a metal thin film. In the case where an electrically insulating substrate is used, for example, in the case where a sapphire substrate or a high-resistance silicon substrate is used, the nitride semiconductor layer may be formed by the same technique, but it is desirable to configure the anode electrode as shown in FIG. 2A to FIG. 2D below.

The anode electrode 10a allows the region including the $Al_xGa_{1-x}N$ layer 11 to absorbs light so as to generate photoexcited carriers (electrons and holes) therein, and contributes to oxidation-reduction reactions through the activity of the carriers. Specifically, upon photoexcitation, the holes generated in the $Al_xGa_{1-x}N$ layer 11 move to the surface of the anode electrode (the surface of the $Al_xGa_{1-x}N$ layer) and oxidizes water in contact with the anode electrode 10a to produce oxygen. That is, the anode electrode 10a itself serves as an oxygen producing electrode. On the other hand, the electrons generated by photoexcitation are not consumed in the anode electrode 10a but are collected in the electrode portion 14 disposed in the anode electrode 10a and supplied to the cathode electrode through a wire that is electrically connected to the anode electrode and the cathode electrode.

Since the band gap of the $Al_xGa_{1-x}N$ layer 11 of the anode electrode 10a is 3.4 eV or more, the anode electrode 10a cannot serve as a light-driven photoelectrode unless it is irradiated with light having a wavelength of at least 360 nm or less. Therefore, for the effective use of light, the composition ratio of aluminum (the value of x) in the $Al_xGa_{1-x}N$ layer 11 ($0<x\leq1$) of the anode electrode 10a is desirably in a range of $0<x\leq0.25$, and particularly desirably in a range of $0.05<x\leq0.15$, except where it is possible to irradiate the anode electrode with light having a wavelength equal to or greater than the band gap of the $Al_xGa_{1-x}N$ layer 11.

When the $Al_xGa_{1-x}N$ layer 11 is irradiated with light having wavelengths in the above range, the absorption region of the $Al_xGa_{1-x}N$ layer 11 has a depth of about 100 nm from the irradiated surface, although it depends on the band gap. Therefore, for the use as a photoelectrode, the thickness of the $Al_xGa_{1-x}N$ layer 11 is desirably 70 nm or more and 1 µm or less, and further desirably 80 nm or more and 200 nm or less.

The $Al_xGa_{1-x}N$ layer 11 is laminated on the GaN layer 12 to efficiently collect the carriers generated by light irradiation of the anode electrode 10a into the electrode portion 14. The GaN layer 12 is desirably n-type or $n^+$-type. Since the n-type or $n^+$-type GaN layer 12 has low electrical resistance, it is effective in reducing the ohmic loss. In this configuration, it is desirable to use a GaN layer doped with an impurity element (such as silicon) and thus having low electrical resistance. This configuration was mainly adopted in the following examples.

Figure 1B:
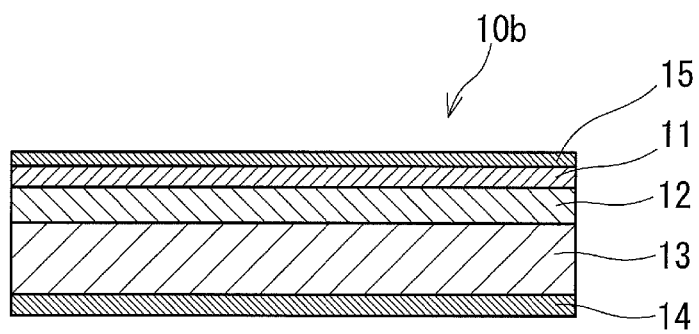

The main configuration of the anode electrode (photoelectrode) according to the present embodiment has been described so far. In order to increase the efficiency of oxygen production as the function of the anode electrode and to increase the durability of the anode electrode, it is also possible to adopt a configuration as shown in FIG. 1B, in which a surface coating layer 15 containing nickel oxide is disposed on the $Al_xGa_{1-x}N$ layer 11 as the surface of the anode electrode without blocking the light irradiation of the $Al_xGa_{1-x}N$ layer 11. This configuration is obtained by using the surface coating layer 15 having a thickness thin enough (for example, 10 nm or less) not to block the light irradiation or having a band gap large enough to reduce absorption of the light.

Figure 1C:
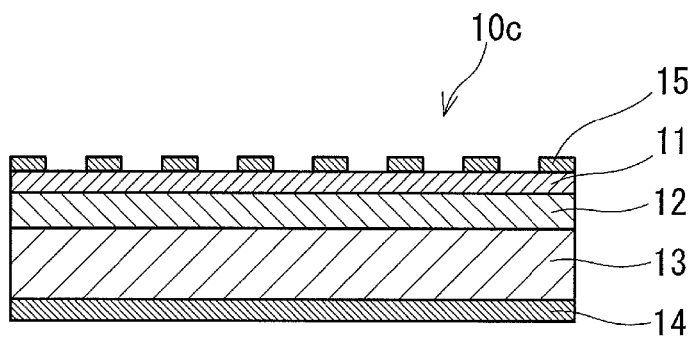
Figure 1D:
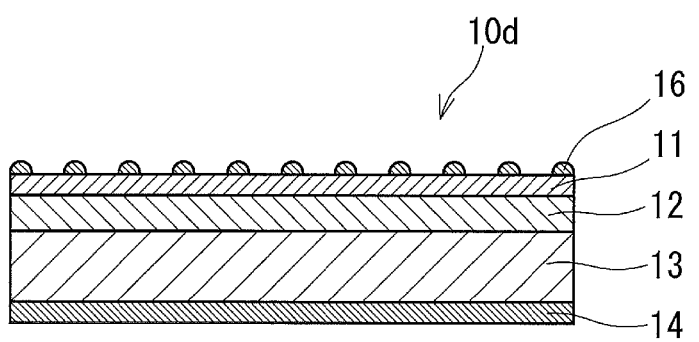

It is also desirable to cut the surface coating layer 15 into pieces and arrange the pieces on the $Al_xGa_{1-x}N$ layer 11 such that part of the surface of the $Al_xGa_{1-x}N$ layer 11 is exposed, as shown in FIG. 1C. In this case, the pieces of the surface coating layer 15 do not necessarily have to have a uniform shape, and the pieces of various shapes and sizes may be arranged in a randomly distributed manner on the surface of the $Al_xGa_{1-x}N$ layer. Furthermore, it is also desirable to provide a configuration as shown in FIG. 1D, in which a large number of nickel oxide fine particles 16 are arranged in a distributed manner on the surface of the $Al_xGa_{1-x}N$ layer 11.

The present inventors have confirmed that in these configurations, the so-called co-catalytic activity of nickel oxide is effective in increasing the oxygen production efficiency at the anode electrode.

FIG. 2A to FIG. 2D are each a schematic configuration view of an anode electrode (photoelectrode) in which a substrate made of an electrically insulating material (insulating substrate 23) is used instead of the conductive substrate in each of the above-described configurations. In each of anode electrodes 20a, 20b, 20c, and 20d shown in FIG. 2A to FIG. 2D, a GaN layer 22 is formed on the insulating substrate 23 and an $Al_xGa_{1-x}N$ layer 21 ($0<x\leq1$) is formed on the GaN layer 22. In addition, each of the anode electrodes 20a to 20d includes an electrode portion 24 on the GaN layer 22 formed on the insulating substrate 23. Specific examples of the insulating substrate 23 include a single-crystalline sapphire substrate. The GaN layer 22 has the same structure as the GaN layer 12, and the $Al_xGa_{1-x}N$ layer 21 ($0<x\leq1$) also has the same structure as the $Al_xGa_{1-x}N$ layer 11 ($0<x\leq1$). Furthermore, in each of the anode electrodes 20b to 20d shown in FIG. 2B to FIG. 2D, a surface coating layer 25 (or nickel oxide fine particles 26) is (are) disposed on the $Al_xGa_{1-x}N$ layer 21. This surface coating layer 25 also has the same structure as the surface coating layer 15 described above. Not only the use of any of the configurations shown in FIG. 1A to FIG. 1D but also the use of any of the configurations shown in FIG. 2A to FIG. 2D makes it possible to form a desired anode electrode (photoelectrode).

(Device for Reducing Carbon Dioxide by Light Energy)

Figure 3:
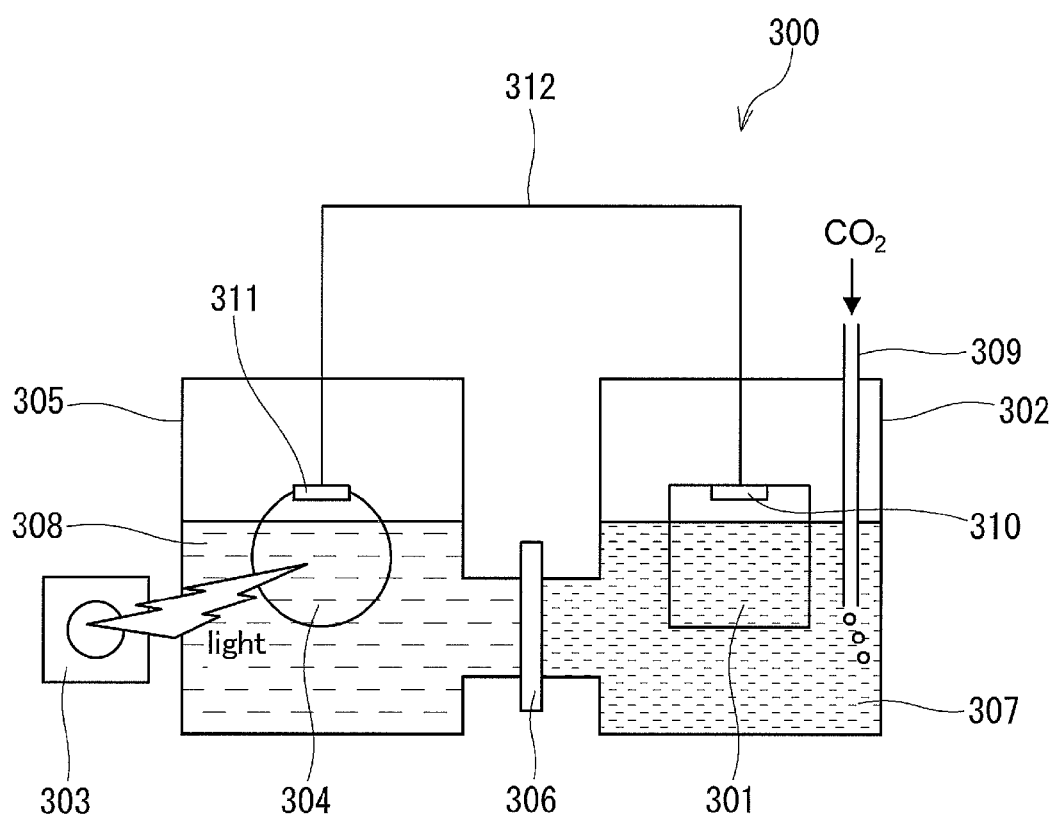
FIG. 3 is a schematic view of a device for producing an alcohol through carbon dioxide reduction reaction driven by light energy according to an embodiment of the present disclosure.

FIG. 3 is a schematic view of an example of an device for producing an alcohol through carbon dioxide reduction driven by light energy. A device 300 includes a cathode chamber 302, an anode chamber 305, and a proton conducting membrane 306.

A first electrolytic solution 307 is contained in the cathode chamber 302, and the cathode chamber 302 contains a cathode electrode 301. The cathode electrode 301 is in contact with the first electrolytic solution 307. Specifically, the cathode electrode 301 is immersed in the first electrolytic solution 307.

The first electrolytic solution 307 is an aqueous potassium chloride solution (aqueous KCl solution) or an aqueous sodium chloride solution (aqueous NaCl solution). The concentration of the first electrolytic solution is desirably 1 mol/L or more, and particularly desirably 3 mol/L or more. The first electrolytic solution 307 contains carbon dioxide (dissolved therein). The concentration of the carbon dioxide contained in the first electrolytic solution is not particularly limited. Desirably, the first electrolytic solution 307 containing carbon dioxide dissolved therein is acidic.

Examples of the material of the cathode electrode 301 at which reduction of carbon dioxide takes place to produce alcohols include metallic materials containing copper (Cu) as a main component and copper compound materials. The cathode electrode 301 may consist of copper or a copper compound material, but may have a laminated structure of a copper-based material layer and a substrate for supporting the copper-based material layer. For example, the cathode electrode 301 may have a structure including a substrate such as glass or glassy carbon (registered trademark) and a thin film of a copper-based material formed on the substrate, or a structure including a conductive substrate and a large number of fine particles of a copper-based material supported on the substrate. The structure of the cathode electrode 301 is not limited as long as the cathode electrode 301 has the capability of reducing carbon dioxide enough to produce alcohols. Only a part of the cathode electrode 301 may be immersed in the first electrolytic solution 307 as long as the material of the cathode electrode 301 is in contact with the first electrolytic solution 307.

A second electrolytic solution 308 is contained in the anode chamber 305, and the anode chamber 305 contains an anode electrode 304. The anode electrode 304 is a photoelectrode that exhibits its activity when irradiated with light. The anode electrode 304 includes a region including a nitride semiconductor formed of a laminate of an $Al_xGa_{1-x}N$ layer ($0<x\leq1$) and a GaN layer. As the anode electrode 304, for example, the anode electrode 10a or the like as described above is used. The anode electrode 304 is in contact with the second electrolytic solution 308. Specifically, the anode electrode 304 is immersed in the second electrolytic solution 308.

The second electrolytic solution 308 is an aqueous sodium hydroxide solution (aqueous NaOH solution). The concentration of the second electrolytic solution is desirably 1 mol/L or more, and particularly desirably about 5 mol/L. Desirably, the second electrolytic solution 308 is basic.

As described later, the region of the anode electrode 304 (photoelectrode) immersed in the second electrolytic solution 308 is irradiated with light having a wavelength of at least 360 nm or less from a light source 303.

In order to separate the first electrolytic solution 307 from the second electrolytic solution 308, the proton conducting membrane 306 is interposed between the cathode chamber 302 and the anode chamber 305. This means that the first electrolytic solution 307 and the second electrolytic solution 308 are not mixed together.

The proton conducting membrane 306 is not particularly limited as long it allows protons to pass therethrough but prevents other substances from passing therethrough. An example of the proton conducting membrane 306 is Nafion (Registered Trademark).

The cathode electrode 301 and the anode electrode 304 have electrode terminals 310 and 311, respectively. These electrode terminals 310 and 311 are electrically connected to each other by a conducting wire 312 without an external power source such as a battery, a solar cell, or a potentiostat. That is, the cathode electrode 301 is electrically connected to the anode electrode 304 through the conducting wire.

(Method for Reducing Carbon Dioxide by Light Energy)

Next, the method for reducing carbon oxide using the above-described device to produce alcohols is described.

A carbon dioxide reduction device 300 can be placed at room temperature and under atmospheric pressure.

As shown in FIG. 3, the anode electrode (photoelectrode) 304 is irradiated with light from the light source 303. An example of the light source 303 is a xenon lamp. The light from the light source 303 has a wavelength of 360 nm or less. Particularly desirably, the light has a wavelength of 250 nm or more and 325 nm or less.

Desirably, the device includes a gas inlet tube 309, as shown in FIG. 3. In the reduction process, it is desirable to reduce carbon dioxide contained in the first electrolytic solution 307 while supplying carbon dioxide into the first electrolytic solution 307 through the gas inlet tube 309. One end of the gas inlet tube 309 is immersed in the first electrolytic solution 307. It is also desirable to supply carbon dioxide into the first electrolytic solution 307 through the gas inlet tube 309 so as to dissolve a sufficient amount of carbon dioxide in the first electrolytic solution 307 before starting the reduction of carbon dioxide.

In the case where the cathode electrode 301 includes a copper-based material, carbon dioxide contained in the first electrolytic solution 307 is reduced by irradiating the anode electrode 304 with light so as to produce not only alcohols but also aldehyde, formic acid, carbon monoxide, hydrocarbon, hydrogen, etc.

EXAMPLES

The present disclosure is described in more detail with reference to the following examples.

Example 1

As a conductive substrate, a low-resistance single-crystalline gallium nitride (GaN) substrate (with a thickness of about 0.4 mm and a diameter of 2 inches) was used. On the substrate, an n-type, low-resistance GaN thin film doped with silicon (with a film thickness of 2.0 μm and a Si doping level of $2.5\times10^{18}$ $cm^{-3}$) and then an undoped $Al_xGa_{1-x}N$ thin film (with a film thickness of 100 nm and an x value of 0.11, i.e., an aluminum composition ratio of 11%) were epitaxially grown by metal-organic vapor-phase epitaxy. Furthermore, a large number of nickel oxide fine particles (with a size of several tens of nanometers to several micrometers) were arranged in a distributed manner on the AlGaN layer of the anode electrode by solution reaction. Then, an electrode layer (with a thickness of about 500 nm) containing titanium (Ti), aluminum (Al), and gold (Au) was formed on the back surface of the GaN substrate. Thus, the anode electrode (photoelectrode) 304, as shown in FIG. 1D, including a conductive substrate, an n-type GaN layer formed on the conductive substrate, an AlGaN layer formed on the n-type GaN layer, and nickel oxide fine particles arranged on the surface of the AlGaN layer so as to coat a part of the surface, was obtained.

As the cathode electrode 301, a copper plate with a thickness of 0.5 mm was used. The copper plate used as the cathode electrode was subjected to treatment for removing an oxide film formed on the surface or etching so as to form a clean copper surface before use. About 4 $cm^2$ of the copper plate was immersed in the first electrolytic solution.

A device for reducing carbon dioxide by light energy, shown in FIG. 3, was fabricated using the anode electrode (photoelectrode) and the cathode electrode prepared as described above. The distance between the anode electrode and the cathode electrode was about 8 cm. The specific configuration of the device was as follows.

First electrolytic solution 307: aqueous potassium chloride solution (aqueous KCl solution in an amount of 180 mL) with a concentration of 3.0 mol/L Second electrolytic solution 308: aqueous sodium hydroxide solution (aqueous NaOH solution in an amount of 180 mL) with a concentration of 5.0 mol/L Proton conducting membrane 306: Nafion membrane "Nafion 117" (DuPont)

Light source 303: xenon lamp (with a power of 300 W, a light irradiation area of about 4 $cm^2$, and an irradiation light power of about 20 $mW/cm^2$)

Carbon dioxide was supplied into the device by bubbling carbon dioxide gas (at a flow rate of 200 mL/min) in the first electrolytic solution 307 for 30 minutes through the gas inlet tube 309. The anode chamber 305 includes a light irradiation window (not shown), and through the light irradiation window, the surface of the anode electrode in which the $Al_xGa_{1-x}N$ layer and the GaN layer were laminated was irradiated with light including ultraviolet light (having a wavelength of 360 nm or less) from the light source 303 for a given period of time.

Comparative Example 1

A device for reducing carbon dioxide was fabricated using the same anode electrode (photoelectrode) and the same cathode electrode as those in Example 1. In this Comparative Example, in order to reduce carbon dioxide, an aqueous potassium bicarbonate solution (aqueous $KHCO_3$ solution) with a concentration of 3.0 mol/L was used as the electrolytic solution contained in the cathode chamber, and the same aqueous sodium hydroxide solution (aqueous NaOH solution) with a concentration of 5.0 mol/L as that used in Example 1 was used as the electrolytic solution contained in the anode chamber. That is, carbon dioxide was reduced in a device configured in exactly the same manner as in Example 1 except for the first electrolytic solution.

The anode electrode (photoelectrode) in the device configured in this manner was irradiated with light from a light source. As a result, in both Example 1 and Comparative Example 1, reaction currents (in an amount of 6 to 12 mA) flowed through the conducting wires. When light irradiation was stopped, no reaction current was observed. This means that some sort of reactions occurred at the anode electrode (photoelectrode) and the cathode electrode by light irradiation.

hol ($CH_3CH_2OH$) and n-propanol ($CH_3CH_2CH_2OH$) were produced in the cathode chamber, although a very small amount of hydrogen ($H_2$) was also evolved through water reduction reaction. The amount of each of these reaction products was proportional to the amount of electric charge (in coulombs) associated with the reaction. Furthermore, in the anode chamber in which the anode electrode was placed, oxygen ($O_2$) in an amount corresponding to the amount of the reaction products obtained in the cathode chamber was evolved through water oxidation reaction.

It was confirmed from these results that light irradiation of the anode electrode caused the cathode electrode (copper electrode) to develop a catalytic reaction to reduce carbon dioxide and part of the reaction contributed to the production of alcohols.

On the other hand, in Comparative Example 1, a reaction current flowed and oxidation-reduction reactions occurred at the anode electrode and the cathode electrode as in Example 1, but no alcohol was detected and only carbon monoxide (CO), formic acid (HCOOH), etc. were obtained as carbon dioxide reduction products.

Table 1 shows the production efficiencies (Faradaic efficiencies) with which the reaction products were obtained in Example 1 and Comparative Example 1. Several experiments were conducted under the same conditions as those in Example 1. As a result, alcohol (ethanol) production efficiencies were 0.6 to 1.7% in Example 1. As used herein, the production efficiency (Faradaic efficiency) means the ratio of the amount of electric charge used to produce each reaction product to the total amount of electric charge obtained by light irradiation, and is expressed by the following equation:

(Production efficiency)=(Amount of electric charge used to produce each reaction product)/(Total amount of electric charge obtained by light irradiation)×100[%]

TABLE 1

| Production efficiency (%) | CO | $CH_4$ | $C_2H_4$ | $C_2H_6$ | HCOOH | $CH_3CHO$ | $CH_3CH_2OH$ | $CH_3CH_2CH_2OH$ |
|---|---|---|---|---|---|---|---|---|
| Example 1 | 41.71 | 0.03 | 2.38 | 0.02 | 17.64 | 1.53 | 1.15 | 1.07 |
| Comparative Example 1 | 1.41 | 0.01 | 0.00 | 0.00 | 29.66 | 0.00 | 0.00 | 0.00 |

In view of the above, the present inventors have further studied these reactions in detail in the following manner. Specifically, after the cathode chamber was sealed (with a specific amount of carbon dioxide contained therein), the anode electrode was irradiated with light for a specific period of time (1 to 3 hours). Then, the reaction products generated in the cathode chamber through carbon dioxide reduction caused by the activity of the cathode electrode were identified and the amounts of these products were measured. Gas components generated in the cathode chamber were analyzed by gas chromatography. Liquid components generated in the cathode chamber were analyzed by liquid chromatography and head-space gas chromatography. Furthermore, the amount of electric charge (in coulombs) associated with the carbon dioxide reduction reaction was calculated from the integrated value of the amount of reaction current obtained by the light irradiation.

As a result, in Example 1, it was confirmed that, as carbon dioxide reduction products, not only carbon monoxide (CO), ethylene ($C_2H_4$), formic acid (HCOOH), and acetaldehyde ($CH_3CHO$) but also alcohol components such as ethyl alco- Example 2

An anode electrode configured as shown in FIG. 1A was prepared without arranging nickel oxide fine particles on the surface of the AlGaN layer of the anode electrode (photoelectrode), and experiments were conducted using this anode electrode in the same manner as in Example 1.

As a result, it was confirmed that alcohols were obtained as carbon dioxide reduction products as in Example 1.

Example 3

Experiments were conducted in the same manner as in Example 1 except that a thin film of $Al_xGa_{1-x}N$ with an aluminum composition ratio (a value of x) of 0.22 instead of 0.11 was formed as an $Al_xGa_{1-x}N$ layer of an anode electrode (photoelectrode).

As a result, it was confirmed that alcohols were also obtained as carbon dioxide reduction products as in Example 1 when the composition ratio of aluminum in the AlGaN layer was changed.

Example 4

Figure 2A:
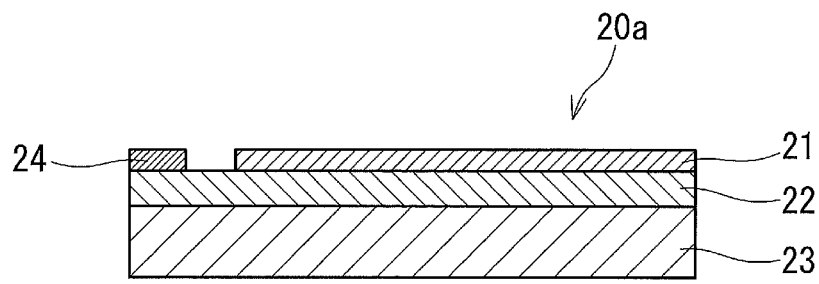
FIG. 2A to FIG. 2D are each a schematic view showing an example of the configuration of another anode electrode (photoelectrode) according to an embodiment of the present disclosure.
Figure 2B:
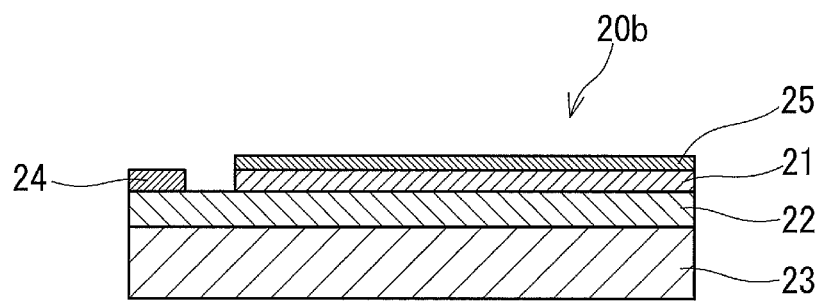
Figure 2C:
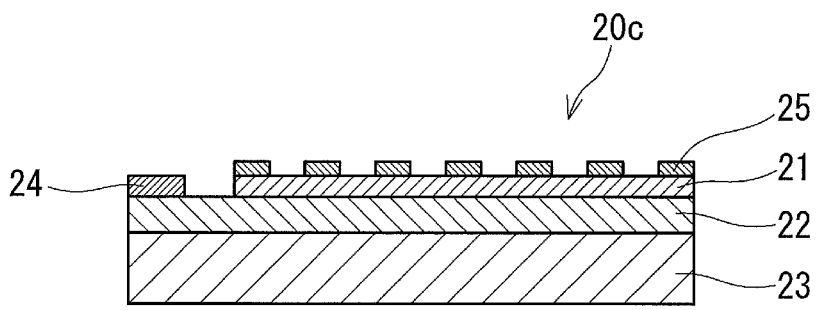
Figure 2D:
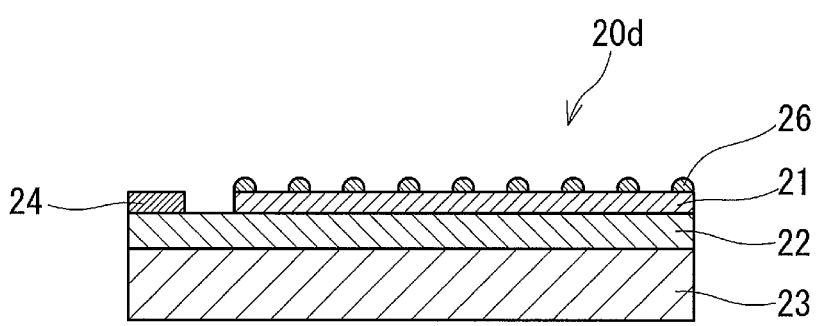

Experiments were conducted in the same manner as in Example 1 except that a single-crystalline sapphire substrate was used as a substrate on which a nitride semiconductor layer was to be formed and an epitaxial growth process was used to form an anode electrode configured as shown in FIG. 2D.

As a result, it was confirmed that alcohols were also obtained as carbon dioxide reduction products as in Example 1 when the anode electrode (photoelectrode) was configured in a different manner so as to form the configuration on an insulating substrate.

Example 5

Experiments were conducted in the same manner as in Example 1 except that a glassy carbon (registered trademark) substrate with copper fine particles supported on the entire surface thereof was used instead of a copper plate as a cathode electrode.

As a result, it was confirmed that almost the same reaction products as those in Example 1 were obtained. In addition, almost the same result was obtained when a copper-nickel alloy containing traces of nickel component was used instead of copper fine particles as the cathode electrode.

Example 6

Experiments were conducted in the same manner as in Example 1 except that an aqueous sodium chloride solution (aqueous NaCl solution) was used instead of an aqueous potassium chloride solution (aqueous KCl solution) as a first electrolytic solution contained in the cathode chamber.

As a result, it was confirmed that alcohols were also obtained as carbon dioxide reduction products when the aqueous sodium chloride solution was used as the first electrolytic solution.

Comparative Example 2

Experiments were conducted in the same manner as in Example 1 except that a mixed solution of an aqueous potassium chloride solution (aqueous KCl solution) and an aqueous potassium bicarbonate solution (aqueous $KHCO_3$ solution) was used as a first electrolytic solution contained in the cathode chamber. The content (volume content) of the aqueous potassium chloride solution in the mixed solution was 33 to 67%.

As a result, although the mixed electrolytic solution contained a potassium chloride component, almost the same carbon dioxide reduction products as those obtained when the aqueous potassium bicarbonate solution was used as the first electrolytic solution (in Comparative Example 1) were obtained. This suggests that an electrolytic solution used to produce alcohols through light-energy driven carbon dioxide reduction needs to contain at least 70% by volume of the aqueous potassium chloride solution component.

Comparative Example 3

Experiments were conducted in the same manner as in Example 1 except that a single-crystalline n-type titania was used instead of a laminate of an AlGaN layer and a GaN layer as an anode electrode (photoelectrode).

As a result, a reaction current was obtained when the titania anode electrode was irradiated with light, but the amount of reaction current obtained was about one tenth that obtained at the anode electrode of the present disclosure. In addition, only hydrogen ($H_2$) was obtained as a reaction product and no product resulting from carbon dioxide reduction reaction was obtained.

As described above, it was confirmed that, in a novel light energy-driven carbon dioxide reduction device including a combination of a anode electrode (photoelectrode) serving as an oxygen producing electrode and a cathode electrode capable of reducing carbon dioxide, alcohols can be produced from carbon dioxide by light irradiation alone. In this novel device, an electrode including a nitride semiconductor region in which an $Al_xGa_{1-x}N$ layer ($0<x\leq1$) and a GaN layer are laminated is used as the anode electrode (photoelectrode), and an aqueous potassium chloride solution or the like with an appropriate concentration is used as the electrolytic solution for the cathode electrode.

The present disclosure may be embodied in other forms without departing from the spirit or essential characteristics thereof. The embodiments disclosed in this specification are to be considered in all respects as illustrative and not limiting. The scope of the present disclosure is indicated by the appended claims rather than by the foregoing description, and all changes which come within the meaning and range of equivalency of the claims are intended to be embraced therein.

INDUSTRIAL APPLICABILITY

The present disclosure provides a novel method for producing alcohols through carbon dioxide reduction reaction driven by light energy.

The technical idea derived from the above disclosure is as follows:

A method for producing an alcohol using a device for reducing carbon dioxide, the method including the steps of:
 (a) preparing the device for reducing carbon dioxide, the device including a cathode chamber (302), an anode chamber (305), and a proton conducting membrane (306), wherein
  the cathode chamber (302) contains a cathode electrode (301),
  the cathode electrode (301) includes copper or a copper compound,
  the anode chamber (305) contains an anode electrode (304),
  the anode electrode (304) includes a region formed of a nitride semiconductor,
  a first electrolytic solution (307) is contained in the cathode chamber (302),
  a second electrolytic solution (308) is contained in the anode chamber (305),
  the cathode electrode (301) is in contact with the first electrolytic solution (307),
  the anode electrode (304) is in contact with the second electrolytic solution (308),
  the proton conducting membrane (306) is interposed between the cathode chamber (302) and the anode chamber (305),
  the first electrolytic solution (307) contains the carbon dioxide,
  the cathode electrode (301) is electrically connected to the anode electrode (304), and
  a power source that is electrically connected to the cathode electrode (301) and the anode electrode (304) is not provided between the cathode electrode (301) and the anode electrode (304), the first electrolytic solution (307) is an aqueous potassium chloride solution or an aqueous sodium chloride solution, and the second electrolytic solution (308) is an aqueous sodium hydroxide solution; and (b) irradiating the region with light having a wavelength of 360 nanometers or less (desirably, 200 nanometers or more and 400 nanometers or less) so as to reduce the carbon dioxide contained in the first electrolytic solution (307) and to produce the alcohol in the first electrolytic solution (307), wherein the cathode electrode (301) does not need to be irradiated with the light.

What is claimed is:

1. A method for producing an alcohol using a device for reducing carbon dioxide by light energy, the method comprising the steps of:

(a) preparing the device for reducing carbon dioxide, the device including a cathode chamber, an anode chamber, and a proton conducting membrane, wherein the cathode chamber contains a cathode electrode, the cathode electrode includes copper or a copper compound, the anode chamber contains an anode electrode, the anode electrode includes a region including a nitride semiconductor layer in which an $Al_xGa_{1-x}N$ layer ($0<x\leq1$) and a GaN layer are laminated, a first electrolytic solution consisting of an aqueous potassium chloride solution (aqueous KCl solution) is contained in the cathode chamber, a second electrolytic solution including an aqueous sodium hydroxide solution (aqueous NaOH solution) is contained in the anode chamber, the cathode electrode is in contact with the first electrolytic solution, the anode electrode is in contact with the second electrolytic solution, the proton conducting membrane is interposed between the cathode chamber and the anode chamber, the first electrolytic solution contains carbon dioxide, the cathode electrode is electrically connected to the anode electrode, and a power source that is electrically connected to the cathode electrode and the anode electrode is not provided between the cathode electrode and the anode electrode; and (b) irradiating the anode electrode with light having a wavelength of 360 nm or less so as to reduce, at the cathode electrode, the carbon dioxide contained in the first electrolytic solution and to produce the alcohol.

2. The method according to claim 1, wherein a composition ratio of aluminum (a value of x) in the $Al_xGa_{1-x}N$ layer ($0<x\leq1$) of the anode electrode is in a range of $0<x<0.25$.

3. The method according to claim 1, wherein the GaN layer of the anode electrode is n-type or $n^+$-type.

4. The method according to claim 1, wherein an entire surface or a part of the surface of the $Al_xGa_{1-x}N$ layer ($0<x\leq1$) of the anode electrode is coated with at least nickel oxide.

5. The method according to claim 4, wherein the nickel oxide is in the form of fine particles.

6. The method according to claim 1, wherein in the step (b), the device for educing carbon dioxide is placed at room temperature and under atmospheric pressure.

7. The method according to claim 1, wherein in the step (b), aldehyde is also obtained.

8. The method according to claim 1, wherein in the step (b), formic acid is also obtained.

9. The method according to claim 1, wherein in the step (b), carbon monoxide is also obtained.

10. The method according to claim 1, wherein in the step (b), hydrocarbon is also obtained.

11. The method according to claim 1, wherein in the step (b), hydrogen is also obtained.

\* \* \* \* \*